US009227072B2

(12) United States Patent
An et al.

(10) Patent No.: US 9,227,072 B2
(45) Date of Patent: Jan. 5, 2016

(54) SYSTEM AND METHODS FOR IMPROVING DEVICE THERAPY USING HEART SOUNDS

(71) Applicant: Cardiac Pacemakers, Inc., St. Paul, MN (US)

(72) Inventors: Qi An, Blaine, MN (US); Barun Maskara, Blaine, MN (US); Pramodsingh Hirasingh Thakur, Woodbury, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 122 days.

(21) Appl. No.: 14/195,436

(22) Filed: Mar. 3, 2014

(65) Prior Publication Data
US 2014/0277238 A1   Sep. 18, 2014

Related U.S. Application Data

(60) Provisional application No. 61/776,943, filed on Mar. 12, 2013.

(51) Int. Cl.
| | |
|---|---|
| *A61N 1/365* | (2006.01) |
| *A61B 5/02* | (2006.01) |
| *A61N 1/368* | (2006.01) |
| *A61N 1/362* | (2006.01) |
| *A61B 5/0452* | (2006.01) |
| *A61B 5/00* | (2006.01) |
| *A61B 5/0205* | (2006.01) |

(52) U.S. Cl.
CPC .......... *A61N 1/3682* (2013.01); *A61B 5/02028* (2013.01); *A61B 5/0452* (2013.01); *A61B 5/4836* (2013.01); *A61B 5/7278* (2013.01); *A61N 1/3627* (2013.01); *A61N 1/36578* (2013.01); *A61N 1/36585* (2013.01); *A61B 5/02055* (2013.01); *A61B 5/686* (2013.01)

(58) Field of Classification Search
CPC .............. A61N 1/3682; A61N 1/3627; A61N 1/36585; A61B 5/02028; A61B 5/0452; A61B 5/4836
See application file for complete search history.

(56) References Cited

U.S. PATENT DOCUMENTS

2012/0296228 A1* 11/2012 Zhang .................. A61B 5/0006
600/513

OTHER PUBLICATIONS

Ahmed, S. Sultan, et al., "Systolic Time Intervals as Measures of the Contractile State of the Left Ventricular Myocardium in Man", Circulation, vol. XLVI, (Sep. 1972) 559-571.
Melzer, C., et al., "Echocardiographic AV-interval optimization in patients with reduced left ventricular function", Cardiovascular Ultrasound, 2:30, (2004) 1-7.

* cited by examiner

*Primary Examiner* — Tammie K Heller
(74) *Attorney, Agent, or Firm* — Schwegman Lundberg & Woessner, P.A.

(57) ABSTRACT

Devices and methods for improving device therapy such as cardiac resynchronization therapy (CRT) by determining a desired value for a device parameter are described. An ambulatory medical device can be configured to detect a heart sound signal and generate one or more heart sound metrics, detect a characteristic indicative of cannon waves, and determine a desired value for a device parameter, such as a timing parameter which can be used to control the delivery of CRT pacing to various heart chambers. The desired device parameter value can be determined using the heart sound metrics and the characteristic indicative of the cannon waves. The ambulatory medical device can program stimulation using the desired device parameter value, and deliver the programmed stimulations to one or more target sites to achieve desired therapeutic effects.

20 Claims, 5 Drawing Sheets

SYSTEM AND METHODS FOR IMPROVING DEVICE THERAPY USING HEART SOUNDS

CLAIM OF PRIORITY

This application claims the benefit of priority under 35 U.S.C. §119(e) of U.S. Provisional Patent Application Ser. No. 61/776,943, filed on Mar. 12, 2013, which is herein incorporated by reference in its entirety.

TECHNICAL FIELD

This document relates generally to medical devices, and more particularly, to systems, devices and methods for improving a device therapy using heart sounds.

BACKGROUND

Congestive heart failure (CHF) is a major health problem and affects over five million people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood.

CHF is usually a chronic condition, but can occur suddenly. It can affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

SUMMARY

CHF can be treated by cardiac pacing therapy. Pacing therapy to promote synchronization of heart chamber contractions for improved cardiac function is generally referred to as cardiac resynchronization therapy (CRT). Ambulatory medical devices such as cardiac pacemakers are capable of delivering CRT by pacing multiple heart chambers. Some ambulatory medical devices can pace the heart chambers in a sequence that causes the heart chambers to contract in synchrony, thereby increasing the pumping power of the heart and delivering more blood to the peripheral tissues of the body. In the case of dyssynchrony of right and left ventricular contractions, a biventricutar pacing therapy can be used to resynchronize the left and right ventricles. Bi-atrial pacing or pacing of ail four heart chambers can also be used.

Improving the CRT therapy by determining desired CRT parameters involves determining desired pacing parameters, such as intervals between pacing pulses delivered to various heart chambers that provide effective CRT delivery. Due to the variation across patient population in their responses to CRT as well as the within-patient variation in optimal CRT setting as a result of, for example, changes in the patient's activity level, disease progression, medication, and general health condition, the patient response to CRT vary; and the therapy parameter need to be timely adjusted to provide and maintain desired cardiac function to the patient.

Some ambulatory medical devices can include one or more diagnostic features such as using a physiologic signal to detect a physiologic event or monitoring a physiologic condition. For example, the physiologic signal can be used to monitor the patient's response to CRT, or to determine desired values of the CRT parameters. The physiologic signal can be affected by confounding events either physiologic or non-physiologic in nature. The confounding events can not indicate the change in cardiac function such as left ventricular contractility, but they can be mis-interpreted by the ambulatory medical device as improved cardiac function, and thereby impacting the patient's response to the CRT therapy. For example, the heart sound can be used to assess the left ventricular contractility. A shorter atrio-ventricular delay (AVD) can be associated with larger amplitude of S1 heart sound. However, CRT with a short AVD can also cause cannon waves, which occur when the atria contract while mitral value and/or tricuspid valve is already closed; that is, when the ventricles are contracting. Cannon waves can introduce high S1 amplitude, which can be mis-interpreted by the device as an indication of improved cardiac contractility. The present inventors have recognized that there remains a need for devices and methods that can automatically improve the device therapy by setting the CRT parameters on an individualized basis, particularly in the presence of confounding events such as cannon waves.

Various examples described herein can help improve the process of improving the device therapy such as cardiac resynchronization therapy (CRT). For example, an ambulatory medical device can detect a heart sound signal and generate one or more heart sound metrics including S1 intensity. A cannon-wave detector can detect a cannon wave characteristic indicative of one or more cannon waves. A therapy adjustment circuit can be configured to determine a desired value for a device parameter, such as a timing parameter which can be used to control the delivery of CRT pacing to various heart chambers. The desired device parameter value can be determined using the heart sound metrics and the cannon wave characteristic. A controller circuit can program stimulations using the desired device parameter value, and a stimulation generation circuit can generate the programmed stimulations and deliver the stimulations to one or more target sites.

A method can include sensing one or more physiologic signals including a heart sound signal, and generating one or more signal metrics from the one or more physiologic signals. The signal metrics can include S1 intensity. The method can include detecting a cannon wave characteristic indicative of cannon waves. By using the heart sound signal metrics and the cannon wave characteristic, the method can determine a desired value for a device parameter, such as a timing parameter which can be used to control the delivery of CRT pacing to various heart chambers. The method can include generating stimulations according to the desired value for the device parameter and delivering the stimulations to the target sites.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various examples are illustrated by way of example in the figures of the accompanying drawings. Such examples are demonstrative and not intended to be exhaustive or exclusive examples of the present subject matter.

DETAILED DESCRIPTION

Disclosed herein are systems, devices and methods for improving a device therapy using multiple sensor metrics. The device therapy can include cardiac pacing therapy provided by an implantable medical device such as a pacemaker or an implantable cardioverter-defibrillator (ICD). The improvement of the cardiac pacing therapy can include determining a desired value for a relative timing between a first event associated with a heart chamber and a second event associated with a different heart chamber, such as intervals between pacing pulses delivered to atria and ventricles that provide effective CRT delivery. The present document discussed methods and devices for programming or reprogramming the device parameters using heart sounds to increase the patient's response to CRT. Some examples are directed to improving the heart-sounds based therapy adjustment in the presence of confounding events such as cannon waves. The methods and devices described herein can also be applicable to programming or reprogramming other device functions pertaining to an implantable medical device, including pacing therapy, defibrillation therapy, neural stimulation therapy, and patient diagnostics and stratifying a patient's risk of developing a disease or a condition, or to monitoring a patient's health status or response to a medical intervention.

Figure 1:
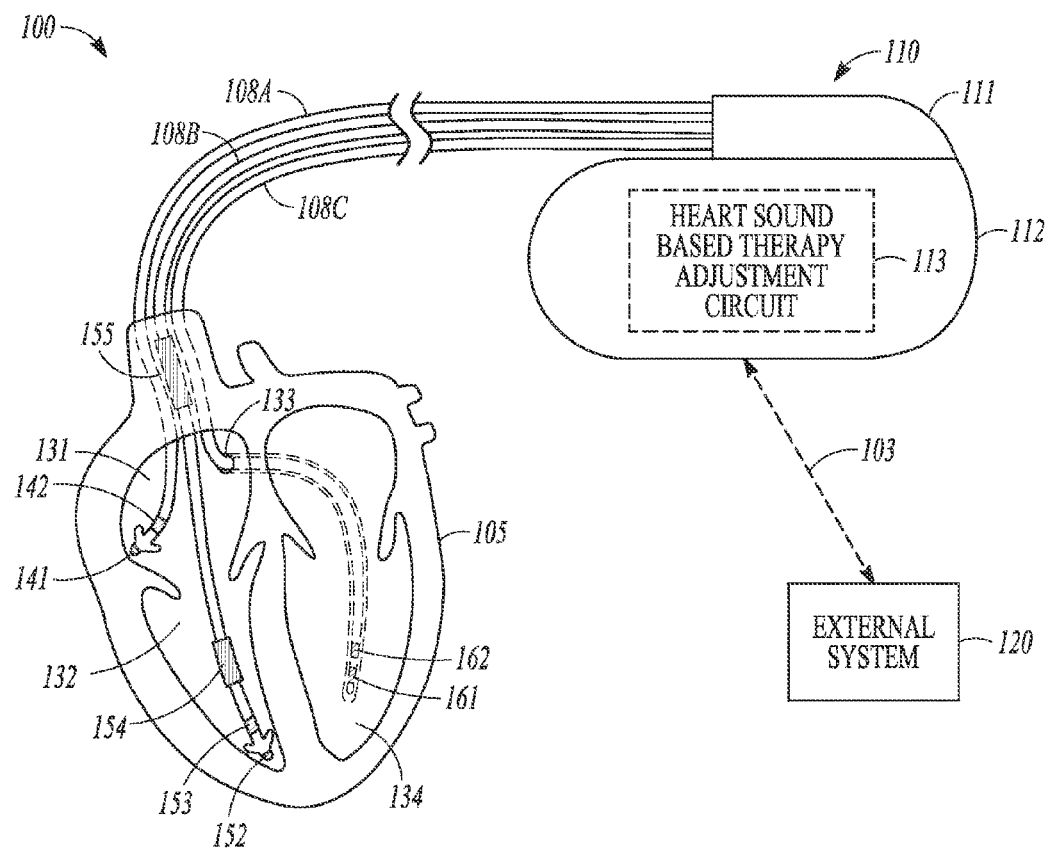
FIG. 1 illustrates an example of cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 1100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 can include an implantable cardiac device such as a pacemaker, an implantable cardioverter-defibrillator (XD), or a cardiac resynchronization therapy (CRT) device. The IMD 110 can include one or more monitoring or therapeutic devices such as a subcutaneously implanted device, a wearable external device, a neural stimulator, a drug delivery device, a biological therapy device, or one or more other ambulatory medical devices. The IMD 110 can be coupled to, or can be substituted by a monitoring medical device such as a bedside or other external monitor.

As illustrated in FIG. 1, the IMD 110 can include a hermetically sealed can 112 that can house an electronic circuit that can sense a physiologic signal in the heart 105 and can deliver one or more therapeutic electrical stimulations to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the MID 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C can be implanted through the coronary sinus 133 and can be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiologic signal. The physiologic signal can include an electrogram or a signal representing mechanical function of the heart 105. The hermetically sealed can 112 can function as an electrode such as for sensing or pulse delivery. For example, an electrode from one or more of the leads 108A-C can be used together with the can 112 such as for unipolar sensing of an electrogram or for delivering one or more pacing pulses. A defibrillation electrode from the lead 108B can be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiologic signal from one or more external physiologic sensors or one or more external electrodes that can be coupled to the IMD 110. Examples of the physiologic signal can include one or more of intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

As illustrated, the CRM system 100 can include a heart sounds based therapy adjustment circuit 113. The heart sounds based therapy adjustment circuit 113 can be configured to improve the therapy such as determining desired values for device parameters used for sensing a physiologic event, providing patient diagnostic information, assessing device operation and functionality, or controlling the generation and delivery of device therapy such as stimulations to the patient. One example of device parameter can include timing of the delivery of pacing pulses to the heart such as an atrial-ventricular delay (AVD). The AVD represents the latency between an intrinsically occurred atrial electrical activation signal (As) such as sensed by the electrodes on the lead 108A and a subsequent ventricular pacing pulse (Vp) such as delivered through the electrodes on the lead 108B, or between an atrial pacing pulse (Ap) such as delivered through the electrodes on lead 108A and the subsequent Vp. In another example, the device parameter can include a left ventricular-right ventricular delay (VVD) which represents the latency between a left ventricular pacing pulse (LVp) such as delivered through the electrodes on the lead 108C and a right ventricular pacing pulse (RVp) such as delivered through the electrodes on the lead 108B. In determining a desired value for a device parameter, the heart sounds based therapy adjustment circuit 113 can be coupled to one or more physiologic sensors or sensing electrodes such as the electrodes on one or more of the leads 108A-C and receive physiologic signals from the physiologic sensors or electrodes. In an example, the IMD 110 can program the stimulations (such as atrial pacing pulses, ventricular pacing pulses, cardioversion pulses, defibrillation pulses, or neural stimulations) and schedule the delivering of the stimulations using the desired device parameter value. Examples of the heart sounds based therapy adjustment circuit 113 are discussed below, such as with reference to FIGS. 2-4.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The heart sounds based therapy adjustment circuit 113 can be implemented at the external system 120, which can be configured to perform target event detection such as using data extracted from the IMD 110 or data stored in a memory within the external system 120. Portions of the heart sounds based therapy adjustment circuit 113 can be distributed between the IMD 110 and the external system 120.

Portions of the IMD 110 or the external system 120 can be implemented using hardware, software, or any combination of hardware and software. Portions of the IMD 110 or the external system 120 can be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals.

Figure 2:
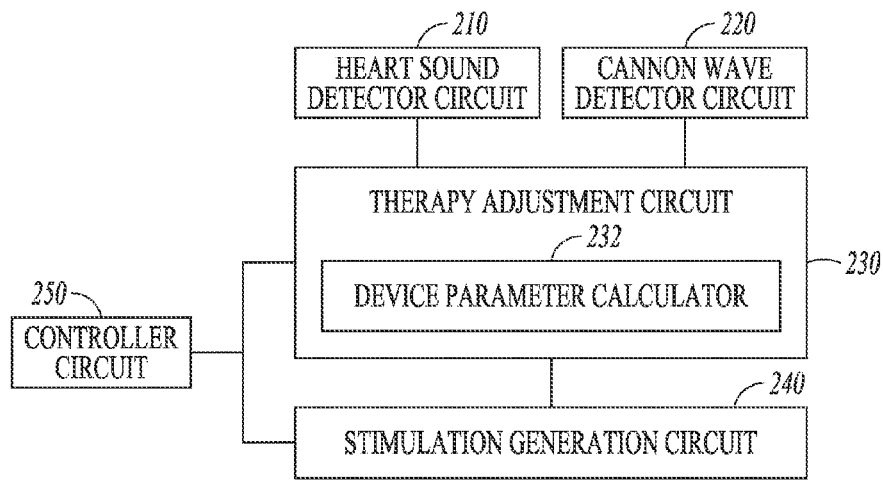
FIG. 2 illustrates an example of a device therapy adjustment circuit.

FIG. 2 illustrates an example of a device therapy adjustment circuit 200, which can be an example of the heart sounds based therapy adjustment circuit 113. The device therapy adjustment circuit 200 can include a heart sound detector circuit 210, a cannon-wave detector circuit 220, a therapy adjustment circuit 230, a stimulation generation circuit 240, and a controller circuit 250.

The heart sound detector circuit 210 can be configured to detect a physiologic signal indicative of heart sounds, and generate one or more heart sound metrics from the heart sound signal. In an example, the heart sound detector circuit 210 can be coupled to a heart sound sensor configured to sense the acoustic wave or mechanical activity in the heart indicative of heart sounds. Examples of the heart sound sensor include a microphone or an accelerometer. The heart sound sensor can be external to the patient or implanted inside the body. In an example, the heart sound sensor can be within an ambulatory medical device such as the IMD 110. The heart sound detector circuit 210 can process the sensed heart sounds through signal amplification, analog to digital conversions, signal filtering, and other signal conditioning processes. From the processed heart sound signal, the heart sound detector circuit 210 can extract one or more heart sound metrics including, for example, S1 intensity, S2 intensity, S3 intensity, or timing metrics of the S1, S2, or S3 heart sound with respect to a fiducial point. In an example, the heart sound metrics can be generated using the heart sound signals and one or more additional signals such as an electrocardiogram (ECG) or an intracardiac electrogram (EGM). The fiducial point used for determining the heart sound timing metrics can include P wave or R wave from the ECG or the EGM. The heart sound metrics can be generated in time domain, frequency domain, or joint time-frequency domain.

The cannon-wave detector circuit 220 can be configured to detect a cannon wave characteristic indicative of one or more cannon waves. The cannon wave characteristic can be detected from a physiologic signal. Examples of the physiologic signal can include ECG, EGM such as that sensed from electrodes on leads 108A-C and the can 112, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature. In an example, the cannon-wave detector circuit 220 can be coupled to one or more electrodes such as on one or more of the leads 108A-C and the can 112. Alternatively or additionally, the signal sensing circuit can be coupled to one or more physiologic sensors configured to sense the one or more physiologic signals. Examples of physiologic sensors include pressure sensors, flow sensors, impedance sensors, accelerometers, microphone sensors, respiration sensors, temperature sensors, and blood chemical sensors. In an example, the cannon wave characteristic can be detected from the heart sound signal detected by the heart sound detector circuit 210. In another example, the cannon wave characteristic can be detected using at least one physiological signal different than the heart sound signal.

In an example, the cannon wave characteristic can include one or more of an onset timing of the cannon waves, an estimated duration of cannon waves, the morphological representation of the cannon waves on a physiologic signal, or an electrical stimulation that induces the cannon waves. In an example, the cannon wave characteristic can include a device parameter associated with the stimulation which can induce cannon waves. For example, the cannon wave characteristic can include an atrio-ventricular delay (AVD) used for controlling the delivery of CRT therapy, where the CRT pacing programmed with a short AVD can induce cannon waves in the patient. Examples of the cannon-wave detector circuit 220 are discussed below, such as with reference to FIGS. 3-4.

The therapy adjustment circuit 230 can be coupled to the heart sound detector circuit 210 and the cannon-wave detector circuit 220. As illustrated in FIG. 2, the therapy adjustment circuit 230 can include a device parameter calculator 232 configured to determine a desired value for a device parameter using the one or more heart sound metrics (such as from the heart sound detector circuit 210) and the cannon wave characteristic (such as from the cannon-waves detector circuit 220). Examples of the device parameter can include parameters used for sensing a physiologic event, providing patient diagnostic information, assessing device operation and functionality, or controlling the generation and delivery of device therapy such as stimulations to the patient. In an example, the therapy adjustment circuit 230 can be configured to determine a desired value for a relative timing between a first event in a first site of the heart and a second event in a second site of the heart, such as an AVD or VVD as used in controlling the CRT therapy. Examples of the therapy adjustment circuit 230 are discussed below, such as with reference to FIGS. 3-4.

The stimulation generation circuit 240 can be configured to generate stimulations for stimulating a target site. In an example, the stimulation generation circuit 240 can generate one or more stimulation trains for stimulating one or more sites of a heart including, for example, a left ventricle, a right ventricle, a left atrium, a right atrium, a pulmonary artery, a septum between the left and right ventricles, and other epicardial or endocardial sites. The stimulation generation circuit 240 can generated one or more stimulation trains for stimulating a neural target including, for example, a baroreceptor regions, nerve trunk, and nerve bundles. The stimulation generation circuit can be coupled to stimulation delivery system which can include one or more of the implantable leads such as 108A-C to deliver the stimulations to the target site.

The controller circuit 250 can be configured to be included with or coupled to the therapy adjustment circuit 230 and the stimulation generation circuit 240. In an example, the controller circuit 250 can be configured to adjust one or more programmable stimulation parameters when certain condition is met. Examples of the stimulation parameters include stimulation pulse strength parameters, pulse waveform or morphology, and stimulation scheduling parameters. The stimulation pulse strength parameters include a pulse amplitude, pulse width, pulse morphology, inter-pulse interval, pulse duty cycle, and pulse frequency. Pulse morphology can include one or more of a square wave, triangle wave, sinusoidal wave, and waves with desired harmonic components to mimic white noise such as indicative of naturally-occurring baroreflex stimulation. The pulses can be of one of multiphasic waves including biphasic, triphasic, or multiphasic waves. The therapy schedule parameters can control the time and duration of the stimulation trains. In an example, the controller circuit 250 can be configured to program the stimulations using the desired device parameter value provided by the therapy adjustment circuit 230 and schedule the output of the stimulations from the stimulation generation circuit 240.

Figure 3:
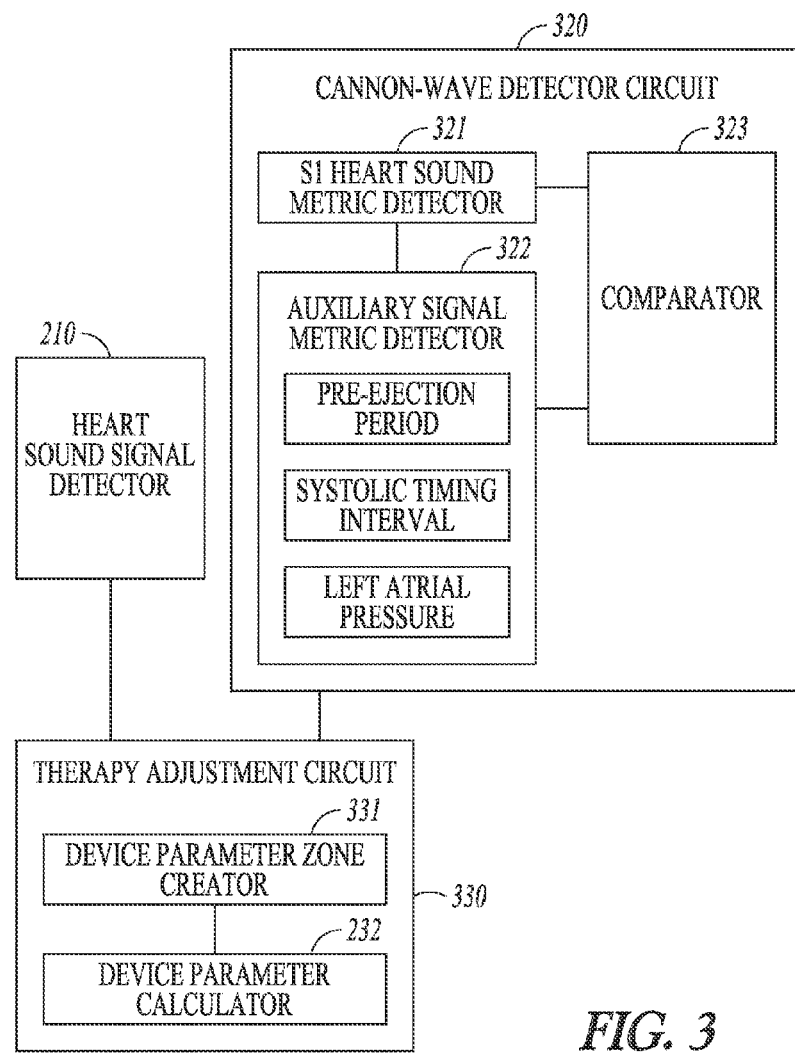
FIG. 3 illustrates an example of the cannon-wave detector and the therapy adjustment circuit as parts of the device therapy adjustment circuit.

FIG. 3 illustrates an example of cannon-wave detector 320 and the therapy adjustment circuit 330 as parts of the device therapy adjustment circuit. The cannon-wave detector 320 can be an example of the cannon-wave detector 220, and the therapy adjustment circuit 330 can be an example of the therapy adjustment circuit 230.

The cannon-wave detector 320 can be configured to determine a threshold value for the device parameter associated with presence of the cannon waves. The cannon-wave detector 320 can include an S1 heart sound metric detector 321, an auxiliary signal metric detector 322, and a comparator 323. The S1 heart sound metric detector 321 can be configured to generate one or more signal metrics associated with S1 heart sound. In an example, the S1 heart sound metrics include S1 intensity (∥S1∥), such as S1 amplitude, S1 power, peak of raw or rectified S1 heart sound, peak-to-peak amplitude of S1 heart sound, energy within a specified time interval around S1 heart sound, energy within a specified frequency range around dominant frequency of the S1, or any measure indicative of the strength of the S1 heart sound.

The auxiliary signal metric detector 322 can be configured to generate one or more signal metric other than the S1 heart sound metrics including, for example, one or more of a pre-ejection period (PEP), a systolic timing interval (STI), and a left atrial pressure (LAP), as illustrated in FIG. 3. The auxiliary signal metrics, such as PEP and STI, are expected to have different responses to the stimulation that cause cannon waves as compared to the S1 intensity. For example, it is expected that in the presence of cannon waves, the S1 intensity can have a sudden and substantial increase while the PEP and STI would not experience such a sudden change.

The PEP represents the total duration of the electrical and mechanical events prior to ejection. The PEP can include the electrical-mechanical delay which occurs between the onset of the ventricular depolarization and the beginning of ventricular contraction, and the isovolumic contraction time during which the left ventricle can contract prior to the opening of the aortic valve. The PEP can be measured using one or more physiologic signals. In an example, the PEP can be measured as the time duration from the onset of the QRS to the S1 heart sound, that is, PEP≈Q–S1 interval. The onset of the QRS can be determined from the ECG as the Q wave or the atrial activation event from the EGM such as the atrial EGM measured using one or more electrodes on the implantable lead 108A and the can 112. The S1 heart sound can be detected from the heart sound signal such as from the heart sound metric detector 321. In another example, the PEP can be measured as the duration from the Q wave or the atrial activation event to the rise of the arterial pressure such as that measured from a carotid pulse wave. In an example, when no spontaneous QRS wave is present and the heart is electrically paced such as by using an IMD 110, the PEP can be measured from the ventricular pacing (Vp) signal to the beginning of ventricular ejection such as represented by the onset of S1 heart sound, that is, PEP≈Vp–S1 interval.

The STI represents the duration of total electro-mechanical systole. The STI spans from the electrical excitation of the heart to the closure of the aortic valve, and it contains two major components, namely the PEP and the left ventricular ejection time (LVET) which represents the time interval from the opening to the closing of the aortic valve (mechanical systole). The STI can be measured using one or more physiologic signals sensed from physiologic sensors. Examples of the physiologic signals used for calculating STI or LVET include a heart sound signal, an intracardiac impedance signal, or a pressure signal. In an example, the STI can be measured as the interval from the onset of the QRS complex on the ECG or the atrial activation event in an intracardiac EGM to the S2 heart sound, that is, STI≈Q–S2 interval. In the case when the ventricle is paced (Vp), the STI can be measured from the ventricular pacing (Vp) signal to the end of ventricular ejection such as represented by the onset of S2 heart sound, that is, STI≈Vp-S2 interval. In an example, the auxiliary signal metric detector 321 can be configured to detect a composite signal metrics, such as PEP/LVET ratio. The LVET can be measured as the duration from the timing of S1 heart sound to a timing of S2 heart sound.

The comparator 323 can be configured to compare the auxiliary signal metric to the S1 intensity (‖S1‖) in response to stimulation with a specified device parameter value, and determine a threshold value for the device parameter using the comparison. In an example, the cannon-wave detector circuit 320 can be configured to determine a threshold value ($AVD_T$) for an atrio-ventricular delay (AVD). The stimulation with an AVD shorter than the threshold $AVD_T$ is likely to cause cannon waves in the heart. In an example, the comparator 323 determines the $AVD_T$ using the comparison between the sensitivity of the S1 intensity to the change in AVD (Δ‖S1‖/ΔAVD) and the sensitivity of the auxiliary signal metric (AUX) to the change in AVD (ΔAUX/ΔAVD). For example, during the delivery of stimulations with gradually decreased AVD values, the S1 heart sound metric detector 321 can detect the S1 intensity, and the auxiliary signal metric detector 322 can detect the auxiliary signal such as PEP or the STI. The comparator 323 can monitor the relationship between Δ‖S1‖/ΔAVD and ΔAUX/ΔAVD, which remains stable until the cannon waves can be induced by stimulation with a short AVD, and causes sudden and significant deviation of the Δ‖S1‖/ΔAVD but no or mild change in ΔAUX/ΔAVD. The comparator 323 can then determine the $AVD_T$ when the covariation between Δ‖S1‖/ΔAVD and ΔAUX/ΔAVD meets a specified criterion such as exceeding a threshold.

In another example, the comparator 323 can monitor and track the changes of the covariation between the S1 intensity and the auxiliary signal metric during the stimulation with gradually decreased AVD values. When the covariation between the S1 intensity and the auxiliary signal metric meets a specified criterion, the cannon wave can be detected; and the resulting AVD can be deemed the threshold $AVD_T$. For example, the comparator 323 determines $AVD_T$ when the ratio of the S1 intensity and the PEP exceeds a specified threshold, i.e., ‖S1‖/PEP>$T_{S1/PEP}$. In an example, the comparator 323 can determine the $AVD_T$ using only the sensitivity of S1 intensity to change in AVD, and determines $AVD_T$ when the resultant sensitivity of the S1 intensity exceeds a specified threshold $T_{S1/\Delta AVD}$, i.e., Δ‖S1‖/ΔAVD>$T_{S1/AVD}$.

In another example, the comparator 323 can determine the $AVD_T$ using the comparison between S1 intensity and the left atrial pressure (LAP). The LAP is expected to increase dramatically in the presence of cannon waves, due to the atrial contraction against a closed mitral valve. The LAP can be measured using a pressure sensor placed in a location close to the atrium, such as in a pulmonary artery, a coronary sinus, or other epicardial or endocrinal locations. The LAP can also be assessed using a physiologic signal indicative of the pressure change including, for example, an impedance measurement using one or more electrodes on an implantable lead such as 108A-C and the IMD can 112. In an example, the comparator 323 can determine the threshold value for the device parameter by comparing the sensitivity of LAP to change in AVD (ΔLAP/ΔAVD) and the sensitivity of S1 intensity to change in AVD (Δ‖S1‖/ΔAVD). For example, during the stimulation to one or more chambers of the heart with gradually decreased AVD values, if Δ‖S1‖/ΔAVD is greater than ΔLAP/ΔAVD by a specified threshold, then the specified AVD causes the changes in myocardial contractility and no cannon waves can be detected. If the difference between Δ‖S1‖/ΔAVD and ΔLAP/ΔAVD at a certain reduced AVD value such falls below a specified threshold, then cannon waves are expected to be induced; and the corresponding AVD can be deemed the threshold value $AVD_T$. In an example, morphology features of the measured LAP signal can be used to determine the presence of cannon wave while gradually varying the AVD value. For example, when cannon waves are induced by pacing with gradually shortened AVD, a c-wave (which corresponds to cannon wave) can be detected in the LAP signal following an a-wave (which corresponds to atrial contraction). A c-wave as detected by morphological analysis of the LAP signal can be used to determine the threshold $AVD_T$.

In an example, the comparator 323 can determine the $AVD_T$ using the comparison between the PEP and the LAP. Because in the presence of cannon waves the LAP is expected to increase dramatically while the PEP would not experience sudden change, the threshold $AVD_T$ can be determined if a relative measure, such as the ratio between LAP and PEP, exceeds a specified threshold, i.e., LAP/PEP>$T_{LAP/PEP}$.

The therapy adjustment circuit 330 can be coupled to the heart sound signal detector 210 and the cannon-wave detector circuit 320, and can include a device parameter zone creator 331 and a device parameter calculator 232. The device parameter zone creator 331 can be configured to determine at least a first device parameter zone and a second device parameter zone using the threshold value for the device parameter. In an example of determining the desired AVD, the device parameter zone creator 331 can receive the threshold $AVD_T$ from the cannon-wave detector circuit 320, and determine at least a first AVD zone characterized by AVD above the threshold $AVD_T$, and a second AVD zone characterized by AVD below the threshold $AVD_T$. Stimulation with the AVD in the first AVD zone is not likely to induce cannon waves; and stimulation with the AVD in the second AVD zone is likely to induce cannon waves. In an example, more than two AVD zones can be created using the $AVD_T$.

The device parameter calculator 232 can be configured to determine the desired value for the device parameter in the first parameter zone using first one or more signal metrics if a first condition is met; or calculate the desired value for the device parameter in the second parameter zone using second one or more signal metrics if a second condition is met. The signal metrics used in the second parameter zone can be different from the signal metrics used in the second parameter zone. In an example, the signal metrics used in the second parameter zone are not identical to the signal metrics used in the first parameter zone but have one or more common signal metrics.

In an example, the device parameter calculator 232 can be configured to determine the desired value for the device parameter by searching, among a plurality of specified values for the device parameter, for one or more values that meet a specified criterion. For example, the device parameter calculator 232 can receive one device parameter value from a device memory at a time and measure the resultant signal metrics such as provide by the heart sound signal detector 210. In an example, the device parameter calculator 232 can use the first one or more signal metrics if the received device parameter value is in the first zone and the second one or more signal metrics if the received device parameter value is in the second zone. For example, the device parameter calculator 232 can measure one or more signal metrics in response to a stimulation programmed with a specified AVD value, and determine the desired AVD value in the first AVD zone (above $AVD_T$) when the S1 intensity is maximized; and determine the desired AVD value in the second AVD zone (below $AVD_T$) when a signal metric different than the S1 intensity meets a specified criterion. Examples of the signal metrics used in the second AVD zone can include S2 intensity, S3 intensity, timing metrics of the S1, S2, or S3 heart sound with respect to a fiducial point, the PEP, the STI, the LAP, or a function of one or more signal metrics herein.

In another example, the device parameter calculator 232 can be configured to adaptively determine the desired value for the device parameter. For example, the device parameter calculator 232 can adjust the value of the device parameter and compare the resultant one or more signal metrics to a convergence criterion. For example, the device parameter calculator 232 can measure one or more signal metrics in response to a sequence of gradually reduced AVD values. The device parameter calculator 232 can determine the desired AVD in the first AVD zone when the resultant S1 intensity can no longer increase beyond a specific threshold, or determine the desired AVD in the second AVD zone when the resultant PEP can no longer decrease beyond a specified threshold, or a function of one or more signal metrics meets a convergence criterion.

Figure 4:
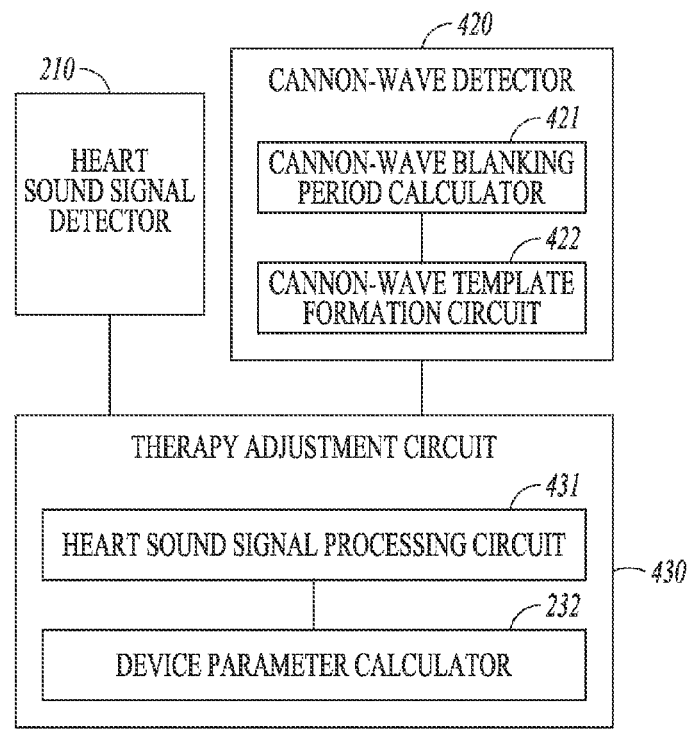
FIG. 4 illustrates an example of the cannon-wave detector and the therapy adjustment circuit as parts of the device therapy adjustment circuit

FIG. 4 illustrates an example of cannon-wave detector 420 and the therapy adjustment circuit 430 as parts of the device therapy adjustment circuit. The cannon-wave detector 420 can be an example of the cannon-wave detector 220, and the therapy adjustment circuit 430 can be an example of the therapy adjustment circuit 230.

The cannon-wave detector 420 can include one or both of a cannon-wave blanking period calculator 421 and a cannon-wave template formation circuit 422. The cannon waves blanking period calculator 421 can be configured estimate a timing of mitral valve closure ($T_{MC}$) and determine a blanking period using the estimated timing $T_{MC}$. The blanking period can be used to blank out a physiologic signal (such as a heart sound signal) during which the cannon waves is present. In an example, the $T_{MC}$ can be estimated as the time instant following the Q wave ($T_Q$) in the ECG or EGM with a specified latency $\Delta_{MC}$, i.e., $T_{MC}=T_Q+\Delta_{MC}$. As an example, $\Delta_{MC}$ can be approximately 100-150 milliseconds. In another example, the $T_{MC}$ can be estimated using the onset of the S1 heart sound when cannon waves are detected, such as by reference of the LAP as provided in the cannon-wave detector circuit 320. The cannon waves blanking period calculator 421 can determine a blanking period from $T_{MC}$ to $T_{MC}+t_W$, where $t_W$ represents a duration of the blanking period. As an example, $t_W$ can be approximately 10-60 milliseconds.

The cannon-wave template formation circuit 422 can be configured to create a cannon-wave template from a physiologic signal. The physiologic signal used for cannon-wave template formation can be from the patient's spontaneously occurred cannon waves, or from the induced cannon waves. In an example, the cannon-wave template formation circuit 422 can create the cannon-wave template from a heart sound signal when cannon waves are known to present, such by inducing the cannon waves with stimulations delivered to the heart with short AVD. The cannon-wave template can include features extracted from a portion of the heart sounds during which cannon waves are present. The features can include statistical features such as peak value, trough value, slope, duration, second and higher-order derivations, and frequency component; morphological features such as representative samples from the heart sound signal or filtered or transformed heart sound signals; or both.

The therapy adjustment circuit 430, coupled to the heart sound signal detector 210 and the cannon-wave detector 420, can include a heart sound signal processing circuit 431 and the device parameter calculator 232. The heart sound signal processing circuit 431 can process the heart sound by removing or lessening the confounding impact of the cannon waves on the heart sound signal provided by the heart sound signal detector 210. In an example, the therapy adjustment circuit 430 can blank the heart sound signal during the blanking period. In another example, the therapy adjustment circuit 430 can filter the heart sound signal using the canon-wave template using a matched filter. The device parameter calculator 232 can receive processed heart sound signal and determine the desired value for the device parameter using the blanked or filtered heart sound signal.

Figure 5:
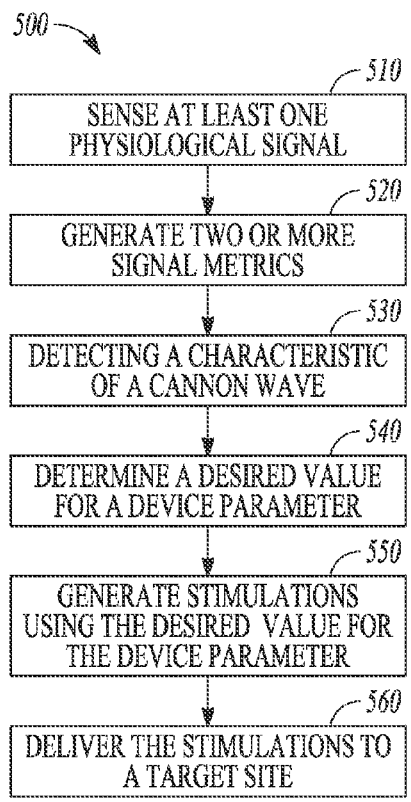
FIG. 5 illustrates an example of a method for determining a desired device parameter and stimulating a target site according to the desired device parameter.

FIG. 5 illustrates an example of a method 500 for determining a desired device parameter and stimulating a target site according to the desired device parameter. In an example, the IMD 110, including its various examples discussed in this document, can be programmed to perform method 500, including its various examples discussed in this document.

In an example, the method 500 can be used to determine a desired value for a relative timing between a first event associated with a first site of the heart and a second event associated with a second site of the heart. One example of the relative timing between the first and the second events can include an atrial-ventricular delay (AVD) which represents the latency between an intrinsically occurred atrial electrical activation signal (As) and a subsequent ventricular pacing pulse (Vp), or between an atrial pacing pulse (Ap) and the subsequent Vp. Another example of the relative timing can include a left ventricular-right ventricular delay (VVD) which represents the latency between a left ventricular pacing pulse (LVp) and the subsequent right ventricular pacing pulse (RVp). The desired value of the AVD or the VVD can then be used to program one or more stimulation trains to be delivered to one or more of the regions in the heart, such as right atrium (RA), left atrium (LA), right ventricle (RV), and left ventricle (LV), so as to restore the synchronization among various sites of the heart.

At least one physiologic signal can be sensed at 510. Examples of the physiologic signal can include ECG, EGM such as that sensed from electrodes on leads 108A-C and the can 112, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature. In an example, the physiologic signals can be acquired by one or more physiologic sensors including, for example, pressure sensors, flow sensors, impedance sensors, accelerometers, microphone sensors, respiration sensors, temperature sensors, and blood chemical sensors.

At 520, two or more signal metrics can be generated from the one or more physiologic signals. In an example, the physiologic signal can be a heart sound signal acquired using an accelerometer sensor, and the heart sound metrics, including S1 intensity, S2 intensity, S3 intensity, or timing metrics of the S1, S2, or S3 heart sound, can be generated from the heart sound signal. In an example, the heart sound metrics can be generated using the heart sound signals and one or more additional signals such as ECG or EGM. In an example, the signal metrics include, for example, a pre-ejection period (PEP), a systolic timing interval (STI), and a left atrial pressure (LAP) which can be measured or calculated from the physiologic signals.

At 530, a cannon wave characteristic can be detected using the two or more signal metrics in the presence of cannon waves. In an example, the cannon wave characteristic can include one or more of an onset timing of the cannon waves, an estimated duration of the cannon waves, morphological representation of the cannon wave on a physiologic signal, and a device parameter associated with the stimulation that induces the cannon waves, such as the atrio-ventricular delay (AVD) or the left ventricular to right ventricular pacing delay (VVD). Examples of the cannon wave characteristic include the heart sound signal metrics (such as the S1 intensity) during the cannon waves and auxiliary signal metrics such as the PEP, STI, and LAP during the cannon waves. The cannon wave characteristic can be detected from a patient's spontaneous cannon waves or from induced cannon waves such as by pacing the heart with a short AVD. Examples of detecting the cannon wave characteristic are discussed below, such as with reference to FIGS. 6-7.

At 540, a desired value for a device parameter can be computed using the signal metrics and the detected cannon wave characteristic. Examples of the device parameter can include parameters used for sensing a physiologic event, providing patient diagnostic information, assessing device operation and functionality, or controlling the generation and delivery of device therapy such as stimulations to the patient. In an example, the device parameter can include a relative timing between a first event in a first site of the heart and a second event in a second site of the heart, such as the AVD and the VVD as used in controlling the CRT therapy.

In an example, the desired value for the device parameter can be determined by searching, among a plurality of values for the device parameter, one or more values that meet a specified criterion such as maximizing a signal metric or a function of one or more signal metrics. In an example, the desired value for the device parameter can be determined adaptively by adjusting the value of the device parameter and comparing the resultant one or more signal metrics or a function of the one or more signal metrics to a convergence criterion. Examples of detecting the cannon wave characteristic are discussed below, such as with reference to FIGS. 6-7.

On or more stimulation trains can then be generated at 550 using the desired value of the device parameter, and delivered to a target site at 560 to achieved, for example, desired treatment. In an example, the stimulation trains can be delivered to one or more regions in a heart including, for example, a left ventricle, a right ventricle, a left atrium, a right atrium, a pulmonary artery, a septum between the left and right ventricles, and other epicardial or endocardial sites. For example, the desired AVD or the desired VVD can be used to program one or more stimulation trains to be delivered to one or more of the regions in the heart, such as right atrium (RA), left atrium (LA), right ventricle (RV), and left ventricle (LV), so as to restore the synchronization among various sites of the heart. The stimulation trains can also be delivered to a neural target which can include a baroreceptor regions, nerve trunk, and nerve bundles.

Figure 6:
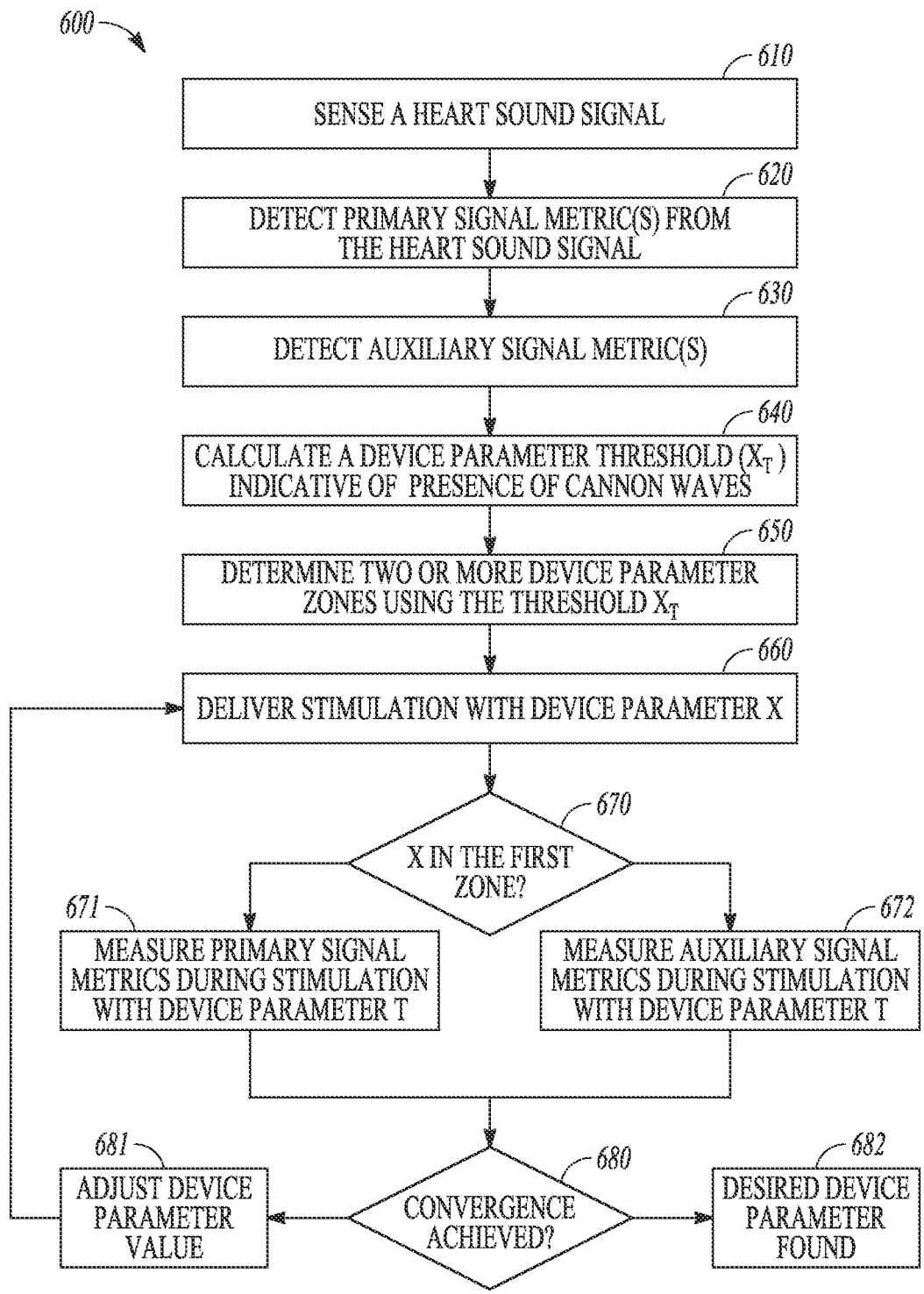
FIG. 6 illustrates an example of a method for determining a desired value for a device parameter using at least two device parameter zones.

FIG. 6 illustrates an example of a method 600 for determining a desired value for a device parameter using at least two device parameter zones. The method 600 can be an example of 500. In an example, the IMD 110, including its various examples discussed in this document, can be programmed to perform method 600, including its various examples discussed in this document.

The heart sound signal can be acquired at 610 using an acoustic sensor such as a microphone or a sensor configured to sense the displacement indicative of heart sound, such as an accelerometer sensor. From the heart sound signal, one or more primary signal metrics can be detected at 620. In an example, the primary signal metrics include the intensity of the S1 heart sound ($\|S1\|$), such as S1 amplitude, S1 power, peak of rectified S1 heart sound, energy within a specified time interval around S1 heart sound, energy within a specified frequency range around dominant frequency of the S1, or any measure indicative of the strength of the S1 heart sound.

At 630, one or more auxiliary signal metrics can be detected from the sensed heart sound signal. Examples of the auxiliary signal metrics include S2 intensity, S3 intensity, or timing metrics of the S1, S2, or S3 heart sound. In an example, the auxiliary signal metrics can be detected from a physiologic signal different than the heart sound signal such as a pressure signal, transthoracic impedance or intracardiac impedance signal, a temperature signal, or other physiologic signals. The signal metrics include, for example, a pre-ejection period (PEP), a systolic timing interval (STI), and a left atrial pressure (LAP) which can be measured or calculated from the physiologic signals. In an example, the auxiliary signal metrics can be generated using a combination of the heart sound signal and one or more additional physiologic signals such as ECG or EGM.

At 640, a device parameter threshold indicative of presence of cannon waves can be calculated. In an example, the threshold value can be determined using the primary signal metrics such as the S1 intensity. For example, it is expected that in the presence of cannon waves the S1 intensity can have a sudden and substantial increase. The threshold value ($AVD_T$) for AVD can be determined when the sensitivity of the S1 intensity to the change in AVD ($\Delta\|S1\|/\Delta AVD$) exceeds a specified threshold $T_{S1/AVD}$, i.e., $\Delta\|S1\|/\Delta AVD > T_{S1/AVD}$. In another example, the threshold can be determined using a comparison of the primary signal metrics and the auxiliary signal metrics (AUX). For example, the covariation between the sensitivity of the S1 intensity ($\Delta\|S1\|/\Delta AVD$) and the sensitivity of the auxiliary signal metrics to the change in AVD ($\Delta AUX/\Delta AVD$) remains stable until the cannon waves occur, which causes significant deviation of the $\Delta\|S1\|/\Delta AVD$ but no or mild change in $\Delta AUX/\Delta AVD$. The $AVD_T$ can be determined if the covariation between $\Delta\|S1\|/\Delta AVD$ and $\Delta AUX/\Delta AVD$ meets a specified criterion such as exceeding a threshold. In another example, the $AVD_T$ can be determined using the comparison between the S1 intensity and the auxiliary signal metric in response to stimulation with gradually decreasing AVD values. For example, the $AVD_T$ can be determined if the ratio between the S1 intensity and the PEP exceeds a specified threshold, i.e., $\|S1\|/PEP > T_{S1/PEP}$.

In another example, the $AVD_T$ can be determined using a comparison between the sensitivity of the S1 intensity to the change of AVD ($\Delta\|S1\|/\Delta AVD$) and the sensitivity of the LAP to the change of AVD ($\Delta LAP/\Delta AVD$). The LAP can be measured using, for example, a pressure sensor placed in a region on or within the heart such as the coronary sinus or pulmonary artery. The LAP can also be assessed using a physiologic signal indicative of the pressure change, such as an impedance measurement across the left atrium. The LAP is expected to increase dramatically in the presence of cannon wave due to the atrial contraction against a closed mitral valve. As a result, during the stimulation to one or more chambers of the heart with a set of gradually decreasing AVD values, if $\Delta\|S1\|/\Delta AVD$ is greater than $\Delta LAP/\Delta AVD$ by a specified amount, then the specified AVD causes the changes in myocardial contractility and no cannon wave can be detected. If $\Delta\|S1\|/\Delta AVD$ is comparable to $\Delta LAP/\Delta AVD$ such that the difference between the two measurements falls below a specified amount, then a cannon wave is expected to present; and the corresponding AVD can be the threshold value $AVD_T$.

At 650, at least a first device parameter zone and a second device parameter zone can be determined using the threshold value for the device parameter. For example, by using the $AVD_T$ two zones can be created, with the first AVD zone being characterized by AVD above the threshold $AVD_T$, and the second AVD zone being characterized by AVD below the threshold $AVD_T$. Stimulation to one or more regions of the heart with the AVD in the first AVD zone is not likely to induce cannon waves; and stimulation to one or more regions of the heart with the AVD in the second AVD zone is likely to induce cannon waves. The two zones can be mutually exclusive, or overlapped. In an example, more than two AVD zones can be created using the $AVD_T$ such that, for example, a first zone can be characterized by AVD above $AVD_T+\delta_1$, a second zone can be characterized by AVD below $AVD_T-\delta_2$, and a third zone characterized by $[AVD_T-\delta_2, AVD_T+\delta_1]$ representing a transitional zone between the first and the second AVD zones.

At 660, stimulation can be programmed with a specified device parameter value and delivered to a target site. The value of the device parameter can be then categorized into one of the device parameter zones at 670. If the device parameter value falls into the first zone, then at 671 the primary signal metrics are measured and used in determining the desired value for the device parameter. If the device parameter value falls into the second zone, then at 672 auxiliary signal metrics are measured and used in determining the desired value for the device parameter. In an example of determining desired AVD, one or more trains of stimulations are delivered to one or more regions of the heart with an initial AVD value $AVD_0$. The initial value $AVD_0$ can be programmed to a default value, such as close to the patient's intrinsic P wave to R wave interval (PR interval) as can be determined from the ECG, or the interval between intrinsic atrial to ventricular interval as can be determined using the sensing electrodes from the leads 108A-C. If the present AVD value is longer than the threshold $AVD_T$ (i.e., in the first AVD zone), then the S1 intensity in response to heart stimulation can be measured. If, however, the present AVD value is shorter than the threshold $AVD_T$ (i.e., in the second AVD zone), then the auxiliary signal metrics, such as S2 intensity, S3 intensity, timing metrics of the S1, S2, or S3 heart sound, PEP, STI, or LAP can be measured.

The measured signal metrics are then assessed at 680 to determine if a convergence criterion is satisfied. In an example, the convergence criterion can include a difference between the present signal metric value $\Omega_k$ and the previous signal metric value $\Omega_{k-1}$ being smaller than a convergence threshold. The present signal metric value $\Omega_k$ corresponds to the present device parameter value such as $AVD_k$, while the previous signal metric value $\Omega_{k-1}$ corresponds to the previous device parameter value such as $AVD_{k-1}$. If the difference between $\Omega_k$ and $\Omega_{k-1}$, defined as $\Delta\Omega = |\Omega_k - \Omega_{k-1}|$, falls below the specified convergence threshold $\Omega_T$, then $\Omega_k$ can be considered converged, and the present device parameter value (for example, $AVD_k$) can be deemed the desired value at 682. Otherwise, the device parameter can be updated at 681. For example, the AVD value can be adjusted using the equation (1):

$$AVD_{k+1} = AVD_k - \alpha^*(\Omega_k - \Omega_{k-1}) \qquad (1)$$

where $\alpha$ can be an positive scalar representing the adaptation rate. According to equation (1), the increment or decrement of the value of the device parameter (for example, AVD) can be controlled by the comparison of $\Omega_k$ and $\Omega_{k-1}$. For example, in the first AVD zone, if $\Delta\Omega$ exceeds a convergence threshold and if $\Omega_k > \Omega_{k-1}$, which suggests that the S1 intensity increases as the AVD changes from $AVD_{k-1}$ to $AVD_k$, then at 681, AVD can be decremented (i.e. $AVD_{k+1} < AVD_k$). If $\Delta\Omega$ exceeds a convergence threshold but $\Omega_k < \Omega_{k-1}$, which suggests that the S1 intensity decreases as the AVD changes from $AVD_{k-1}$ to $AVD_k$, then at 681, AVD can be incremented (i.e. $AVD_{k+1} > AVD_k$). Because the update of AVD can be proportional to $\Delta\Omega$, as the $\Omega_k$ gets closer to $\Omega_{k-1}$, the AVD gets fine-tuned to avoid missing the desired AVD due to a too large increment or decrement. The adjusted device parameter can then be used in generating stimulation and deliver the stimulation to the target site at 660, and the process continues until the convergence condition is met.

Figure 7:
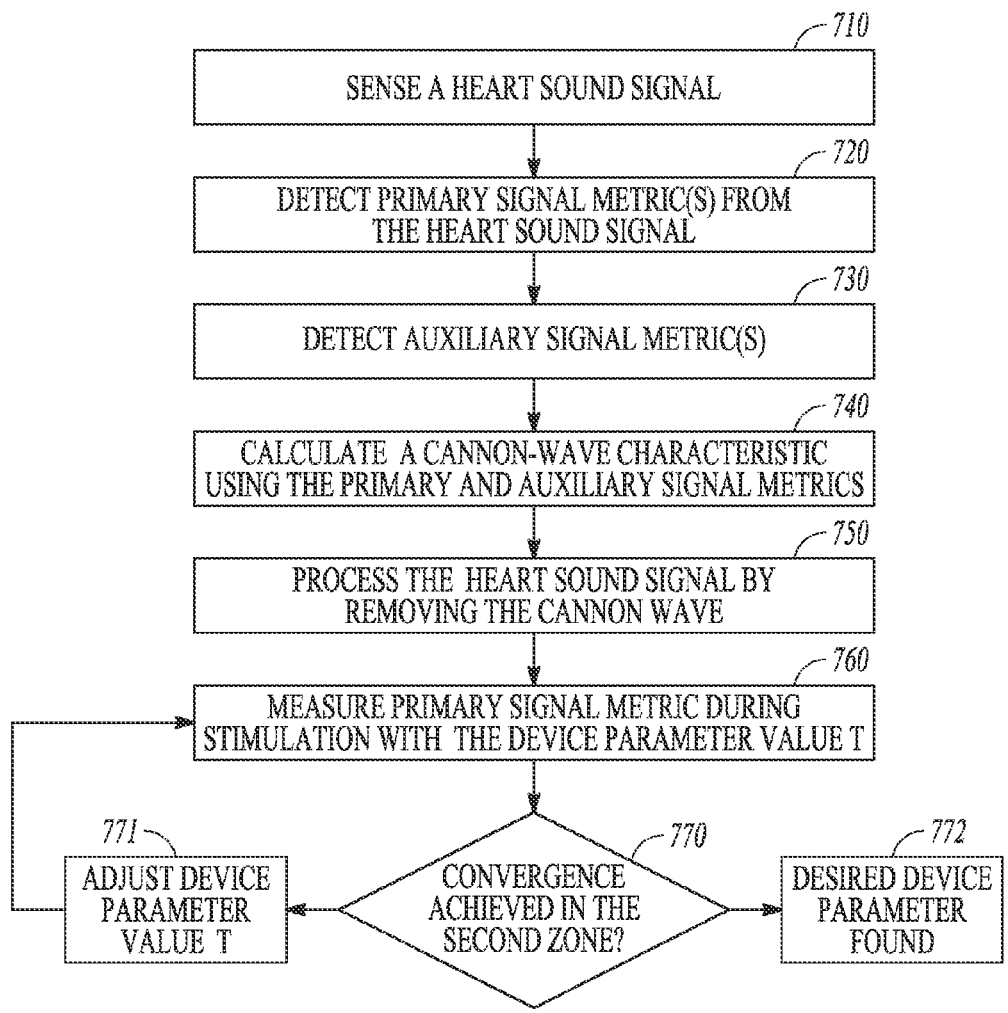
FIG. 7 illustrates an example of a method for determining a desired value for a device parameter using a cannon-wave characteristic.

FIG. 7 illustrates an example of a method 700 for determining a desired value for a device parameter using a cannon wave characteristic. The method 700 can be an example of 500. In an embodiment, the IMD 110, including its various embodiments discussed in this document, can be programmed to perform method 700, including its various embodiments discussed in this document.

The heart sound signal can be acquired at 710 and two or more heart sound signal metrics can be detected from the heart sound signal at 720. Similar to method 600, one or more auxiliary signal metrics can be detected from the heart sound signal or from one or more physiologic signals other than the heart sound signal. At 740, a cannon wave characteristic can be computed using the heart sound signal metrics and the auxiliary signal metrics. In an example, the cannon wave characteristic can include a timing of mitral valve closure ($T_{MC}$) and a blanking period using the timing $T_{MC}$. The blanking period can be used to blank out a physiologic signal (such as a heart sound signal) during which the cannon wave is present. In an example, the $T_{MC}$ can be estimated as the time instant following the Q wave ($T_Q$) in the ECG or EGM with a specified latency $\Delta_{MC}$, i.e., $T_{MC}=T_Q+\Delta_{MC}$. As an example, $\Delta_{MC}$ can be approximately 100-150 milliseconds. In another example, the $T_{MC}$ can be estimated using the onset of the S1 heart sound when a cannon wave is detected, such as by comparing the primary signal metrics (e.g., S1 intensity) and the auxiliary signal metrics (e.g., PEP, STI, or LAP), as discussed in 640. The blanking period can thus be determined as $[T_{MC}, T_{MC}+t_W]$, where $t_W$ can be a specified duration of the blanking period. As an example, $t_W$ can be approximately 10-60 milliseconds.

In another example, the cannon wave characteristic can include a cannon-wave template constructed from a physiologic signal. The physiologic signal used for cannon-wave template formation can be from the patient's spontaneously occurred cannon waves, or from the induced cannon waves. In an example, the cannon-wave template can be formed from the heart sound signal when cannon wave is known to present, such by inducing the cannon wave with stimulations delivered to the heart with a short AVD. The cannon wave template can include features extracted from a portion of the heart sounds. The features can include statistical features such as peak value, trough value, slope, duration, and frequency component; morphological features such as representative samples from the heart sound signal or filtered or transformed heart sound signals; or both.

The heart sound signal can then be processed at 750 by removing or lessening the confounding impact of the cannon wave on the heart sound signal. In an example, the heart sound signal can be blanked out during the blanking period such that heart sounds signal is not sensed and therefore not usable during this period. In another example, the canon-wave template can be used to form a matched filter to filter out the cannon-wave component from the heart sound signal. For example, the cannon-wave can be detected by correlating the heart sound signal to the cannon-wave template. The detected cannon-wave component can subsequently be subtracted from the heart sound signal. Then at 760, the primary signal metrics (such as S1 intensity) can be measured during the stimulation when the device parameter is programmed to an initial value such as $AVD_0$. The initial value $AVD_0$ can be programmed to a default value, such as close to the patient's intrinsic PR interval.

At 770, the primary signal metrics are then assessed at 770 to determine if a convergence criterion is satisfied. In an example, the present S1 intensity ($\|S1\|_k$) measured during stimulation with $AVD_k$ can be compared to $\|S1\|_{k-1}$, measured during stimulation with $AVD_{k-1}$. If the difference $\Delta\|S1\|=|\|S1\|_k-\|S1\|_{k-1}|$ falls below the specified convergence threshold $\|S1\|_T$, then $\|S1\|_k$ can be considered converged, and the present $AVD_k$ can be deemed the desired value at 772. Otherwise, the AVD can be updated at 771. For example, the AVD value can be adjusted using equation (2):

$$AVD_{k+1}=AVD_k-\alpha*(\|S1\|_k-\|S1\|_{k-1}) \quad (2)$$

where $\alpha$ can be an positive scalar representing the adaptation rate. The adjusted device parameter can then be used in generating stimulation and deliver the stimulation to the target site at 760, and the process continues until the convergence condition is met.

The above detailed description includes references to the accompanying drawings, which form a part of the detailed description. The drawings show, by way of illustration, specific embodiments in which the invention can be practiced. These embodiments are also referred to herein as "examples."

Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An ambulatory medical device, comprising:
a stimulation generation circuit configured to generate stimulations for stimulating one or more target sites;
a heart sound detector circuit configured to sense a heart sound signal and generate one or more heart sound metrics including S1 intensity;
a cannon-wave detector circuit configured to detect a cannon wave characteristic indicative of one or more cannon waves;
a therapy adjustment circuit configured to determine a desired value for a device parameter using the one or more heart sound metrics and the cannon wave characteristic; and
a controller circuit configured to be included with or coupled to the therapy adjustment circuit and the stimulation generation circuit, the controller circuit configured to program the stimulations using the desired value for the device parameter and to schedule the delivery of the stimulations to the one or more target sites.

2. The medical device of claim 1, wherein the stimulation generation circuit is configured to generate stimulations for stimulating one or more regions of a heart, and the therapy adjustment circuit is configured to determine the desired value for a relative timing between a first event in a first site of the heart and a second event in a second site of the heart.

3. The medical device of claim 1, wherein:
the cannon-wave detector circuit is configured to determine a threshold for the device parameter associated with presence of the cannon waves; and
the therapy adjustment circuit is configured to:
determine at least a first device parameter zone and a second device parameter zone using the threshold for the device parameter,
calculate the desired value for the device parameter in the first parameter zone using first one or more signal metrics in response to a first condition being met; and
calculate the desired value for the device parameter in the second parameter zone using second one or more signal metrics in response to a second condition being met, the second one or more signal metrics being non-identical to the first one or more signal metrics.

4. The medical device of claim 3, wherein:
the cannon-wave detector circuit is configured to determine a threshold ($AVD_T$) for an atrio-ventricular delay (AVD), a stimulation of one or more regions of a heart programmed with an AVD below the threshold $AVD_T$ able to cause the cannon waves; and
the therapy adjustment circuit is configured to determine a first AVD zone characterized by AVD being above the threshold $AVD_T$, and a second AVD zone characterized by AVD being below the threshold $AVD_T$.

5. The medical device of claim 4, wherein the therapy adjustment circuit is configured to calculate the desired AVD value in the first AVD zone using the S1 intensity, and calculate the desired AVD value in the second AVD zone using a heart sound metric including at least one of S2 intensity, S3 intensity, or a heart sound metric representing relative timing of S1, S2 or S3 heart sound with respect to a fiducial point.

6. The medical device of claim 4, wherein:
the cannon-wave detector circuit comprises an auxiliary signal metric detector configured to detect an auxiliary signal metric, the cannon-wave detector circuit configured to determine the threshold $AVD_T$ using a comparison between the S1 intensity in response to the stimulation and the auxiliary signal metric in response to the stimulation; and
the therapy adjustment circuit is configured to determine the desired AVD value in the second AVD zone using a combination of the S1 intensity and the auxiliary signal metric.

7. The medical device of claim 6, wherein the auxiliary signal metric detector is configured to detect one or more auxiliary signal metrics indicative of a pre-ejection period (PEP), a systolic timing interval (STI), a left ventricular ejection time (LVET), or a composite auxiliary signal metric using at least two auxiliary signal metrics indicative of the PEP, the STI, and the LVET.

8. The medical device of claim 6, wherein the auxiliary signal metric detector is configured to detect an auxiliary signal metric indicative of a left-atrial pressure.

9. The medical device of claim 1, wherein the cannon-wave detector circuit is configured to estimate a timing of mitral valve closure and determine a blanking period using the estimated timing, and the therapy adjustment circuit is configured to blank the heart sound signal during the blanking period, and determine the desired value for the device parameter using the blanked heart sound signal.

10. The medical device of claim 1, wherein the cannon-wave detector circuit is configured to create a cannon-wave template, and the therapy adjustment circuit is configured to process the heart sound signal using the canon wave template, and determine the desired value for the device parameter using the processed heart sound signal.

11. A method for providing a device therapy, comprising:
sensing one or more physiologic signals including a heart sound signal, and generating one or more signal metrics from the one or more physiologic signals, the one or more signal metrics including S1 intensity;
detecting a cannon wave characteristic indicative of one or more cannon waves;
determining a desired value for a device parameter using the one or more signal metrics and the cannon wave characteristic;
generating stimulations using the desired value for the device parameter; and
delivering the stimulations to one or more target sites.

12. The method of claim 11, wherein determining the desired value for the device parameter includes determining a desired value for a relative timing between a first event in a first site of a heart and a second event in a second site of the heart.

13. The method of claim 12, wherein:
detecting the cannon wave characteristic includes determining a threshold ($AVD_T$) for an atrio-ventricular delay (AVD), a stimulation of one or more regions of a heart programmed with the threshold for the AVD able to cause the cannon waves; and
determining the desired value for the device parameter includes:
adjusting the AVD and stimulating the one or more regions of the heart according to the adjusted AVD;
in response to the adjusted AVD exceeding the threshold $AVD_T$, measuring the S1 intensity during the stimulation and determining a desired AVD corresponding to a stimulation that maximizes the S1 intensity; and
in response to the adjusted AVD falling below the threshold $AVD_T$, calculating an auxiliary signal metric different than the S1 intensity and determining the desired AVD corresponding to a stimulation that causes the auxiliary signal metric to meet a specified criterion.

14. The method of claim 13, wherein determining the threshold $AVD_T$ includes:
  measuring the S1 intensity and calculating the auxiliary signal metric during the stimulation to one or more regions of the heart, the stimulation programmed with gradually decreased AVD values; and
  determining the threshold $AVD_T$ using a comparison between a change in the S1 intensity in response to the stimulation and a change in the auxiliary signal metric in response to the stimulation.

15. The method of claim 14, wherein calculating the auxiliary signal metric includes calculating one or more of S2 intensity, S3 intensity, and a signal metric representing relative timing of S1, S2, or S3 heart sound with respect to a fiducial point.

16. The method of claim 14, wherein calculating the auxiliary signal metric includes detecting one or more auxiliary signal metrics indicative of a pre-ejection period (PEP), a systolic timing interval (STI), a left ventricular ejection time (LVET), or a composite auxiliary signal metric using at least two auxiliary signal metrics indicative of the PEP, the STI, and the LVET.

17. The method of claim 14, wherein calculating the auxiliary signal metric includes detecting an auxiliary signal metric indicative of a left-atrial pressure.

18. The method of claim 13, wherein determining the desired AVD in response to the adjusted AVD falling below the threshold $AVD_T$ includes:
  adjusting the AVD and measuring a function constructed using the S1 intensity and at least one auxiliary signal metric different than the S1 intensity during the stimulation according to the adjusted AVD; and
  determining the desired AVD when the measured function meets a convergence criterion.

19. The method of claim 13, wherein detecting the cannon wave characteristic includes estimating a timing of mitral valve closure, and determining the desired value for the device parameter includes:
  determining a blanking period using the timing of the mitral valve closure;
  adjusting the AVD and stimulating the one or more regions of the heart according to the adjusted AVD;
  blanking the heart sound signal during the blanking period; and
  determining the desired AVD using the blanked heart sound signal.

20. The method of claim 13, wherein detecting the cannon wave characteristic includes generating a cannon-wave template, and determining the desired value for the device parameter includes:
  adjusting the AVD and stimulating the one or more regions of the heart according to the adjusted AVD;
  processing the heart sound signal to remove or lessen the cannon-wave from the heart sound signal using the cannon-wave template; and
  determining the desired AVD using the processed heart sound signal.

* * * * *